United States Patent [19]

Marx et al.

[11] 4,111,198

[45] Sep. 5, 1978

[54] AUTOMATED INTRAVENOUS FLUID REGULATING AND ADMINISTERING APPARATUS

[75] Inventors: Alvin J. Marx, 315 College Rd., Bronx, N.Y. 10471; Abraham Edelman, New York, N.Y.

[73] Assignee: Alvin J. Marx

[21] Appl. No.: 802,891

[22] Filed: Jun. 2, 1977

[51] Int. Cl.² .............................................. A61M 5/16
[52] U.S. Cl. ....................... 128/214 E; 128/DIG. 13
[58] Field of Search .................. 128/214 E, DIG. 12, 128/DIG. 13, 214 F

[56] References Cited

U.S. PATENT DOCUMENTS

| | | | |
|---|---|---|---|
| 3,319,623 | 5/1967 | London | 128/214 E |
| 3,601,124 | 8/1971 | Petree | 128/214 E |
| 3,609,379 | 9/1971 | Hildebrandt | 128/214 E |
| 3,631,890 | 1/1972 | Lopin | 128/419 PG |
| 3,655,095 | 4/1972 | Kienitz | 128/214 E |
| 3,736,930 | 6/1973 | Georgi | 128/214 E |
| 3,890,968 | 6/1975 | Pierce | 128/214 G |

*Primary Examiner*—William E. Kamm

[57] ABSTRACT

Automated intravenous fluid dispensing apparatus regulating intravenously administered electrolyte solution, nutrient or other fluid flow employs a bidirectionally motor-driven clamp for selectively constricting a fluid passing conduit, typically a tube. The apparatus employs a relaxation oscillator, or timing circuit, having a variable period dependent upon whether fluid is being administered at a specified rate, or too rapidly or too slowly. When either of the latter two conditions obtain, the tube pinch-off motor is excited in an appropriate corrective direction to cause the desired fluid flow rate.

In accordance with varying aspects of the present invention, motor and timing circuit modulation (i.e., speed of system correction response) varies for excess/-deficient flow rate conditions depending upon the specified flow rate and upon the constrictive state of the fluid delivery tubing. Also, audio/visual alarming is provided for defined conditions.

11 Claims, 3 Drawing Figures

AUTOMATED INTRAVENOUS FLUID REGULATING AND ADMINISTERING APPARATUS

DISCLOSURE OF INVENTION

This invention relates to medical electronics and, more specifically, to improved intravenous flow regulation apparatus.

Intravenous administration of nutrients, electrolyte solution, and/or the like has long been a matter of common practice. Typically, such a fluid delivery system comprises a cascaded source container, drop chamber, tubing and administrating needle. The desired fluid delivery rate, physician prescribed in drops per unit of time, may vary over a relatively wide range. The flow rate is essentially determined by the hydrostatic head (fluid source elevation less the non-constant venous back pressure at the needle aperture which rapidly and markedly changes with patient position and the like), and the tube flow resistance. A tube partial pinch-off clamp is employed to partially constrict the tubing, and comprises the principal fluid metering mechanism.

In manual intravenous administering apparatus, a nurse or other attendant manually adjust the constricting clamp and visually counts drops over a measured time interval until the desired flow rate is attained. Where automated such apparatus is employed, fluid rate is regulated to the prescribed rate, as by automated clamp adjustment or by affirmatively developing the desired flow rate (e.g., by a positive displacement pump).

It is an object of the present invention to provide improved intravenous fluid administering apparatus.

More specifically, it is an object of the present invention to provide improved automated intravenous injection apparatus which can control fluid administration rate over wide bounds; and which operates in a gated feedback mode to give rise to and maintain the proper flow rate.

The above and other objects of the present invention are realized in specific illustrative automated intravenous fluid administration apparatus which regulates fluid flow, employing a bidirectional motor-driven clamp for selectively constricting a fluid passing tube. The apparatus employs a relaxation oscillator, or timing circuit, having a variable period dependent upon whether fluid is being administered at a specified rate, or too rapidly or too slowly. When either of the latter two conditions obtain, the tube pinch-off motor is excited in an appropriate corrective direction to cause the desired fluid flow rate.

In accordance with varying aspects of the present invention, motor and timing circuit modulation (i.e., speed of system correction response) varies for excess/-deficient flow rate conditions (corresponding to early/-late drop arrival) depending upon the specified flow rate and upon the constrictive state of the fluid delivery tubing.

The above and other features and advantages of the present invention will become more clear from the following detailed description of a specific illustrative embodiment thereof, presented hereinbelow in conjunction with the accompanying drawing, in which.

Figure 1:
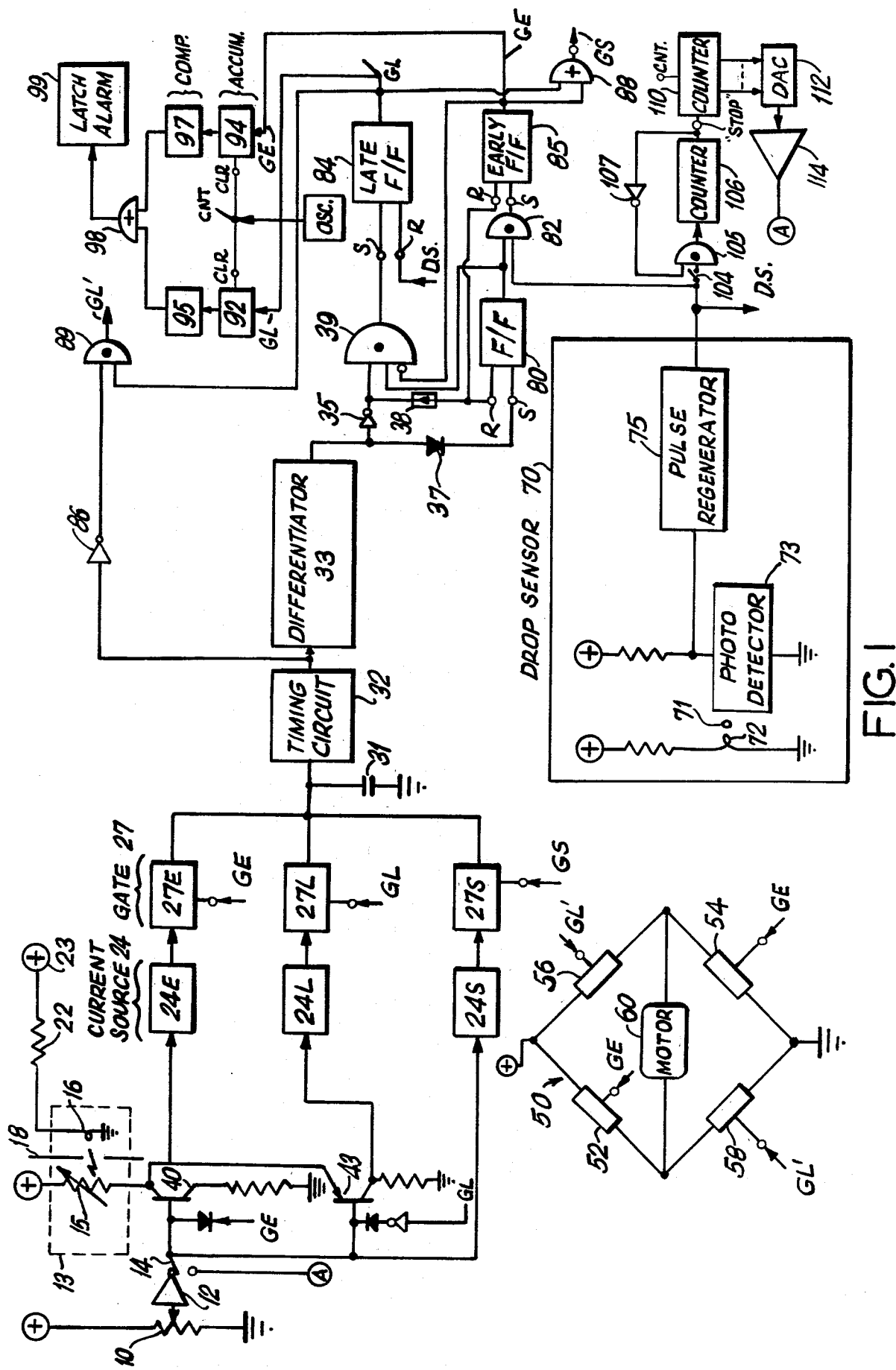
FIG. 1 is a schematic diagram of automated intravenous fluid administering apparatus in accordance with the principles of the present invention.

Referring now to FIG. 1, there is schematically shown automated, regulated apparatus for intravenously injecting electrolyte solution, nutrients, or the like into a patient, the rate of administration (typically measured in drops per unit of time) being specified by the setting of an input potentiometer 10. In overview, the apparatus employs a bidirectionally operative motor 60 which drives a clamping mechanism, as by a worm gear (as per se well known and thus not shown), to partially pinch off fluid delivering tubing to a proper degree such that the actual, sensed fluid drop rate is precisely that specified by the potentiometer 10. To the extent that the actual sensed drop rate deviates materially from the specified rate, the FIG. 1 apparatus more fully discussed below causes the motor 60 to turn in a direction, and in an amount, to cause the proper fluid flow rate by varying the inner delivery tube cross sectional area, and thus its flow resistance. Obviously, the motor 60 moves in a direction to unconstrict the tubing, i.e., create a larger inner cross section, if drops are flowing at an insufficient rate, and to move in a direction to further pinch off the tube (reduce its inner cross sectional area) if fluid is flowing too quickly. In accordance with varying aspects of the invention, corrections are implemented at a varying rate, depending upon the fluid rate flow specified by potentiometer 10, and also depending upon the instantly obtaining degree of tube constriction as sensed by a sensor 13 therefore (schematically depicted in FIG. 1, and in more detail in FIG. 2).

Fluid flow rate measuring signals are developed by a drop sensor 70 which supplies a pulse signalling the incidence of each drop at the drop sensing chamber. The drop sensor 70 employs a light source (e.g., a lamp or light emitting diode 72 energized by a voltage source, and a photodetector 73 (e.g., a photodiode to measure light received from the source 72. When a fluid drop 71 passes in the drop chamber between the source 72 and detector 73, it causes a momentary pulse perturbation or reduction in the light arriving at detector 73, thereby producing an electrical pulse at the terminals of the device 73. This pulse is regenerated and shape-squared in a pulse regenerator 75 of any known form, e.g., a saturated amplifier or a biased monostable trigger circuit.

Figure 2:
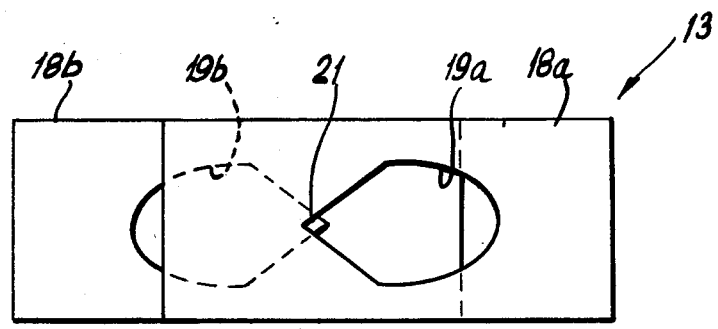
FIG. 2 is a plan view of a light sensing transducer 13 employed in the instant invention to measure the degree of constriction of a intravenous fluid flow administering tube.

As a further signalling transducer element employed in the present invention, tube constriction status transducer 13 shown in FIGS. 1 and 2 is employed to supply electrical signal indicating the degree of constriction of the fluid passing tube. The sensor 13 employs a light source 16 and light sensitive photoresistor 15 separated by an aperture 21 between two light obstructing elements 18a and 18b. The elements 18a and 18b are respectively mechanically fixed for translation with the tube pinch-off elements, or its driver, the elements 18a and 18b respectively including apertures 19a and 19b. The light passing path from light source 16 to variable resistor 15 depends upon the common portion 21 of apertures 19a and 19b, the net effect being that the light impinging on resistor 15 and thus its electrical resistance varies with the degree of constriction of the tubing. The resistance value of resistor 15 is inversely proportional to the amount of light arriving through common aperture portion 21 and, accordingly, the resistance value of resistance 15 increases with tube constriction.

Figure 3:
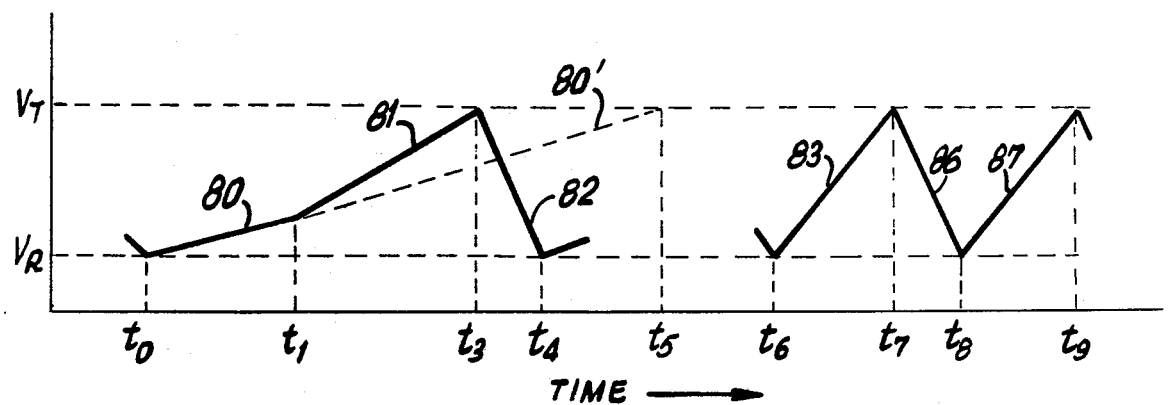
FIG. 3 is a timing diagram illustrating operation of the present invention.

Further by way of overview and preliminary discussion, a timing diagram characterizing operation of the instant invention is shown in FIG. 3. At the beginning of a relaxation oscillator timing cycle, the relaxation oscillator (formed by capacitor 31 charged by one of current sources 24E, 24L, or 24S, and level triggering circuit 32 in FIG. 1) is shown beginning at a time $t_0$. The composite oscillator begins a capacitor 31 charging cycle at a rate given by curve 80–80' corresponding to a standard (S) value which assumes that fluid is being administered at a proper rate, i.e., that for the rate specified by the setting of input potentiometer 10. The charging capacitor 31 will not reach the triggering voltage level $V_t$ until about a time $t_5$ when the next drop would be expected. Assume, however, that the next drop arrives early (E), e.g. at a time $t_1$ rather than about the time $t_5$. When this obtains, the relaxation oscillator is gated to operate at a different (typically more rapid) rate, shown by the curve segment 81, to reach the firing threshold at time $t_3$. During the time $t_1$–$t_3$, the motor 60 is energized (bridge circuit 50 in FIG. 1) in a direction to further close off the tube, thereby lessening delivery rate. The slope of the curve 81, and thereby also the active period for motor 60 actuation, is dependent upon such factors as the prescribed fluid flow rate, the present effective cross sectional tube area, and the degree of excess flow (amount of time the drop is early). Following the time $t_3$ the circuit resets and begins another timing operation.

The curve at the right portion of FIG. 3 characterizes circuit functioning when an insufficient fluid flow is being administered, i.e., when the drop sensor 70 supplies pulses which are "late" (L). During a time interval $t_6$–$t_7$, the controlling relaxation oscillator operates with a slope 83 again depending upon the parameters discussed. During the flyback interval $t_7$–$t_8$ the motor 60 is being energized in a direction to further open the tubing to correct the late drop arrival, insufficient flow rate condition. The motor activated periods 86, . . . , recur until the proper, sufficient flow rate is achieved.

With the above functional overview in mind and returning to the FIG. 1 schematic diagram, the circuitry shown employs a variable frequency oscillator comprising the timing capacitor 31 charged by a selected one of the current sources 24E, 24L or 24S via an associated gate 27E, 27L or 27S, and a threshold timing trigger circuit 32 which fires when the capacitor 31 obtains the threshold voltage value $V_t$. Various embodiments of the timing circuit 32 are well known to those skilled in the art, e.g., a Signetics 555 integrated circuit unit, unijunction transistor circuit, Schmit trigger, and so forth. In particular, the gate 27E is selected by a control pulse GE to charge capacitor 31 at a rate dependent upon the current supplied by the source 24E thereof when the circuit has determined that drops are arriving early corresponding to too rapid a flow administration rate. Similarly, current source 24L is selected by an operative control signal GL opening gate 27L when drops are late, corresponding to too slow a delivery rate; and the current source 24S is selected by gate 27S and control signal GS when the circuit is operating at the specified rate entered into the system by the positioning of the tap at potentiometer 10.

When the too rapid, early condition obtains, the active GE pulse activates controlled switches 52 and 54 (e.g., power transistors or the like) in the bridge 50 to actuate the motor 60 in a direction to drive the tube pinch off clamp to a more closed position, as above discussed. Correspondingly, during late insufficient rate conditions, a modified active GL' signal activates switches 56 and 58 in the bridge 50 to energize motor 60 in an opposite direction to relieve the tube constricting condition, thereby increasing flow rate.

The rate specified at potentiometer 10 is buffered in amplifier 12 and supplied as a current controlling input signal to controlled current source 24S. The voltage-to-current converting source 24S may comprise any embodiment well known therefor, e.g., a simple voltage applied to the base of a transistor having an emitter resistor thereby producing a current substantially equal to the ratio of the applied voltage (less the base-emitted diode drop) and emitter resistance; voltage applied to the inverting input of operational amplifier having a feedback resistance connecting the output and inverting input; or the like. The output of buffer amplifier 12 is also applied to the base of transistors 40 and 43, respectively associated with and gated on during early and late drop conditions via per se gating diodes, the transistors 40 and 43 similarly being controlled by the respective control signals GE and GL. For "early" or too rapid a flow rate condition processing, the potentiometer 10 specified rate produces a current in transistor 40 substantially proportional to the base voltage applied to the transistor 40, producing a voltage at the transistor 40 collector dependent upon the product of this current and the resistive state of variable resistor 15, thereby also depending upon the degree of pinch off of the tube. The resulting potential is applied to voltage-to-current converter 24E which passes, during early condition processing, through gate 27E to the capacitor 31.

When a late condition obtains, transistor 43 is activated by the GL gate pulse to supply current source 24L with a control potential which is effectively determined by the ratio of the amplifier 12 output potential divided by the resistance of variable resistance 15 (which now serves as an emitter resistance), multiplied by the collector resistance of the transistor 43.

The pulses present at the output of timing circuit 32 during flyback restoring period (times $t_3$–$t_4$, $t_7$–$t_8$, . . . , of FIG. 3), assumed low state, are differentiated by differentiator 33, and the negative pulses inverted by inverter 35. The positive differentiated output pulses are selected by positively poled diode 37. Accordingly, at the times $t_3$, $t_7$, . . . , at the beginning of a flyback period, pulses are present at the output of inverter 35 for the assumed timer 32 - differentiator 33 operation, while pulses are present at the output of a diode 37 at the end of the flyback interval, i.e., at the times $t_4$, $t_8$, . . . , . It is observed that the assumed wave polarity output of circuit 32 may be derived for any timing circuit implementation, simply employing an inverter if required.

Consider first the case where fluid is being administered at too rapid a rate, i.e., the case above considered with respect to the left portion of FIG. 3. Following the time $t_0$, the circuitry of FIG. 1 presumes that the apparatus is properly administering fluid at the specified or standard rate, and thus capacitor 31 charges at the normalized rate of the curve 80, as determined by the output of current source 24S passing through the now GS signal-enabled gate 27S. The gate 27S is enabled by the GS signal developed at the output of an OR-NOT gate 89 which is activated when early condition signalling flip-flop 85 is reset, and a GL signal supplying AND gate 88 is inactive by reason of the high output of timing circuit 32 inverted by inverter 86. At the time $t_1$, the drop sensor 70 reports that it has sensed a next drop at the time $t_1$ shown in FIG. 3 which is too early, i.e., which occurs before the composite relaxation oscillator has timed out (reached its threshold voltage V$t$).

When this occurs, the output pulse from drop sensor 70 activates one input of AND gate 82, the other input of which is enabled by the output of a flip-flop 80 which was previously set by the output of a diode 37 substantially at the time $t_o$. The output of AND gate 82 sets the early flip-flop 85 signalling an early drop condition (too rapid a fluid flow). The now set early flop-flop 85 produces an active GE output pulse, shutting down the GS output of OR-NOT gate 89. The active GE signal gates on the current source 24E thus, for example, more rapidly charging capacitor 31 as shown by the curve 81 in FIG. 3 (the source 24S being blocked by the now disabled GS pulse thus deactivating gate 27S). The active GE control signal also enables gated switches 52 and 54, turning on the motor 60 in a direction to close down the tube pinching clamp as long as the GE signal persists.

At the time $t_3$ shown in FIG. 3, the capacitor 31 reaches its threshold value, firing circuit 32. This produces an assumed negative-going pulse at the output of differentiator 33 substantially at the time $t_3$ which passes through the inverter 35, resetting the flip-flops 80 and 85 after a small delay effected by delay circuit 38. The reset flip-flop 85 turns off the GE signal, hence again creating an active standard control pulse GS to initiate another cycle after flyback. If the drop is still too early on the next cycle, the motor will again be turned on and the process will repeat until the proper tube cross sectional value for current conditions is obtained.

Similar operation occurs for an insufficient flow or late drop condition as shown by the right portion of FIG. 3. Assuming time out of the relaxation oscillator with no encountered drop, the differentiated pulse passed by inverter 35 upon time out will fully enable the gate 39 which has its other inputs enabled by the set flip-flop 80 (set by diode 37 at the inception of the last timing cycle) and by the absence of a GE signal at the inverting input of the gate 39. Accordingly, the gate 39 sets the late flip-flop 84 producing an active GL signal which suppresses development of the standard signal GS. The active GL signal causes capacitor 31 charging with the slope 85 depending upon output of the current source 24L. The set late flip-flop 84 also enables an AND gate 89 which is fully switched by the inverter 86 inverted outputs of time 32 during flyback periods 86, . . . , to open bridge gates 56 and 58 via pulses GL' to cause motor energization in a direction to open the pinched off tubing to increase the rate of fluid flow. The late drop flip-flop 84 will remain set until a drop is sensed by drop sensor 70.

The above described arrangement has thus been shown to automatically produce an intravenous fluid flow of a value specified by a signal entered at potentiometer 10, and to implement such corrections as may from time-to-time be necessary to maintain the desired rate should the flow deviate from the specified value. It will be appreciated that in actual application, some fluid flow correction will be substantially continuously required since a shifting patient's body posture will cause substantial variations in the body fluid entry back pressure.

Several ancillary matters are here noted. First, it is desirable in the application of intravenous feeding apparatus to provide for audio and/or visual alarming for defined conditions, e.g., non-controlled conditions characterized by excessive early (GE) or late (GL') pulses. To this end, accumulators 92 and 94 are provided to respectively provide output voltage states which reflect accumulations of the GE and GL' pulses. Comparators 95 and 97 sense the accumulation state of accumulators 92 and 94, respectively. When the state of the accumulators 92 and 94 exceed predetermined bounds as sensed by a comparator 95 or 97, the comparator supplies an off-normal range output which passes through an OR gate 98 to enable a latching audio and/or visual alarm 99. A time base oscillator 90 is provided to periodically clear accumulators 92 and 94. Accordingly, the out-of-range definition for excessive GE or GL pulses is predicated on the basis of the number of such pulses exceeding a maximum permissible value therefor within the period between consecutive output pulses from the time base oscillator 90.

Particular embodiments for the accumulators 92 and 94 and comparators 95 and 97 are per se well known to those skilled in the art, and may be implemented on either an analog or digital basis. More specifically, an analog accumulator may comprise a capacitor having the charge therein increased responsive to each input pulse, and where each comparator may simply comprise a difference amplifier or the like comparing the charge state of the accumulator-capacitor with a reference voltage such as supplied at the output of potentiometer. The capacitor may be cleared by simply using the pulse output of the time base oscillator 90 to trigger a silicon controlled rectifier or the like connected in parallel with the capacitor, the rectifier extinguishing itself once the capacitor is discharged. Alternatively, a digital accumulator may simply comprise a counter having its outputs connected to a digital comparator which provides an output indication when the contents of such a counter exceed the contents of the fixed or adjustable register.

It is also noted that it is sometimes desirable to adjust the composite FIG. 1 arrangement to simply preserve whatever rate of intravenous administration was theretofore being manually implemented. To this end, the attendant simply closes a switch 104 to supply a pulse responsive to each drop from sensor 70 through an initially enabled AND gate 105 and a counter 106. An initially cleared counter 110 counts output pulses from a time base source, e.g., the oscillator 90. When the counter 106 counts a preset number of intravenous fluid drops, it stops and latches the counter 110, while blocking the AND gate 105 via an inverter 107, thereby also latching up the counter 106. Accordingly, the contents of counter 110, driven by the fixed rate source, contains a measure of the rate at which the drop sensor 70 was supplying drops. The output of counter 110 is converted to a rate control voltage via a digital-to-analog converter 112, is buffered by an amplifier 114, and becomes an alternate input via a switch 14 in place of the rate otherwise manually inserted into the composite FIG. 1 apparatus by the potentiometer 10 as above discussed.

The above described arrangement is merely illustrative of the principles of the present invention and numerous modifications and adaptations thereof will be readily apparent to those skilled in the art without departing from the spirit and scope of the present invention.

What is claimed is:

1. In combination in intravenous fluid regulator apparatus, timing circuit means including a timing capacitor, plural current sources, plural controlled gate means each selectively connecting an associated current source with said timing capacitor, fluid drop sensing means, and logic means having plural inputs connected to said fluid drop sensing means and to said timing means and plural outputs each connected to a different one of said controlled gate means for selectively enabling said gate means.

2. A combination as in claim 1 further comprising driven fluid conduit constricting means, and circuit means connected to said logic means for selectively bidirectionally energizing said driven conduit constricting means.

3. A combination as in claim 2 wherein said circuit means includes a bridge having controlled switch means connected to said plural outputs of said logic means.

4. A combination as in claim 1 wherein said plural current sources include an excess fluid rate current source and a deficient rate current source, said logic means including means for enabling said gate means associated with said excess rate current source responsive to said drop sensing means sensing an early fluid drop and means for enabling said gate means associated with said deficient fluid rate current source responsive to said drop sensing means detecting a late fluid drop.

5. A combination as in claim 4 further comprising rate specifying means for specifying a desired fluid administration rate, said excess and said deficient rate current sources including means for supplying a current depending upon the output of said rate specifying means.

6. A combination as in claim 5 further comprising transducer means for signalling fluid delivery system constriction, said excess and said deficient rate current sources including means for supplying a current depending upon the output of said transducer means.

7. A combination as in claim 4 further comprising transducer means for signalling fluid delivery system constriction, said excess and said deficient rate current sources including means for supplying a current deending upon the output of said transducer means.

8. A combination as in claim 5 wherein said rate specifying means comprises means for measuring an obtaining intravenous fluid flow rate and for providing an output signal indicative thereof.

9. A combination as in claim 8 wherein said rate measuring means comprises time base means, a counter for counting output pulses from said time base means, drop counting means, and means responsive to said drop counting means for latching said counter means.

10. A combination as in claim 1 further comprising alarming means connected to said logic means for signaling an off-normal alarm condition.

11. A combination as in claim 10 wherein said logic means comprises insufficient and excess flow condition signaling pulse sources, and wherein said alarming means comprises cascaded accumulator means, comparator means, and latching alarm means.

* * * * *